United States Patent [19]

Bremmer et al.

[11] 4,365,073
[45] Dec. 21, 1982

[54] DERIVATIVES OF CYANO-SUBSTITUTED KETONES AND ALDEHYDES

[75] Inventors: Bart J. Bremmer, Ashland, Mass.; Robert L. Reierson, Midland, Mich.

[73] Assignee: The Dow Chemical Company, Midland, Mich.

[21] Appl. No.: 198,572

[22] Filed: Oct. 20, 1980

[51] Int. Cl.³ .................. C07D 317/10; C07D 319/04
[52] U.S. Cl. ..................................... 549/451; 549/372
[58] Field of Search ............... 260/340.7, 340.9 R; 549/372, 451

[56] References Cited

U.S. PATENT DOCUMENTS

| | | | |
|---|---|---|---|
| 2,435,869 | 2/1948 | Brusen | 260/464 |
| 2,447,975 | 8/1948 | Croxall | 260/338 |
| 2,495,214 | 1/1950 | Crews | 260/404 |
| 3,138,616 | 6/1964 | Scotti et al. | 260/340.9 R |
| 3,169,879 | 2/1965 | Wahl et al. | 260/340.7 |
| 3,714,196 | 1/1973 | Bondler et al. | 260/340.9 R |
| 3,928,406 | 12/1975 | Leeper et al. | 260/340.7 |
| 4,031,112 | 6/1977 | Oppenlaender | 260/340.7 |
| 4,077,982 | 3/1978 | Young et al. | 260/340.7 |
| 4,098,815 | 7/1978 | Babej et al. | 562/503 |
| 4,105,687 | 8/1978 | Suzuki | 260/465.4 |
| 4,207,088 | 6/1980 | Konz | 549/453 |
| 4,320,024 | 3/1982 | Reierson et al. | 252/78.1 |

FOREIGN PATENT DOCUMENTS 187038 12/1966 U.S.S.R. ................. 260/340.9 R

OTHER PUBLICATIONS

Boekelheide et al., Journ. Amer. Chem. Soc. 71, Oct. '49, pp. 3303–3307.
Deuchert et al., Chem. Ber. 112, 2045–2061 (1979).

Primary Examiner—Ethel G. Love
Attorney, Agent, or Firm—Douglas N. Deline

[57] ABSTRACT

Novel cyano- and hydroxyl-substituted cyclic compounds of the formula:

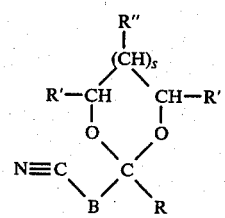

wherein B, R, R' and R" are named substituents are disclosed.

8 Claims, No Drawings

DERIVATIVES OF CYANO-SUBSTITUTED KETONES AND ALDEHYDES

BACKGROUND OF THE INVENTION

In Soviet Union Pat. No. 569,575, published Oct. 12, 1977, certain 2-cyano-substituted dioxolane compounds are disclosed. Further ring-substituted derivatives were not taught. The compounds were reportedly used as fillers for electrically insulating bitumen lacquer impregnates.

Fischer and Smith, J. Org. Chem., 25, 319–324 (1960) disclosed the formation of 2-vinyl-4-hydroxymethyl-1,3-dioxolane and 2(2-cyanoethyl)-4,4,6-trimethyl-1,3-dioxane. Derivatives containing hydroxy or hydroxyalkyl substituents or further derivatives thereof in addition to cyanoalkyl substituents were not produced.

SUMMARY OF THE INVENTION

According to the invention are produced cyanoalkyl-substituted cyclic compounds or mixtures thereof of the formula:

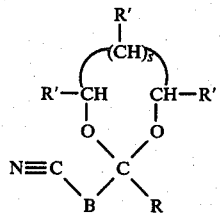
(I)

wherein

R is hydrogen, phenyl, or a monovalent radical of from 1 to 10 carbons selected from branched or linear alkyl and cyano-, hydroxy-, alkoxy-, acyloxy- or organosiloxy-substituted derivatives thereof;

B is a divalent radical of from 2 to 10 carbons selected from the group consisting of branched or linear alkylene and $-(CH_2)_m+OCH_2CH(R_1)+_n$ where m and n are integers equal to or greater than one, $R_1$ is hydrogen, methyl or ethyl;

R' independently each occurrence is selected from the group consisting of hydrogen, and

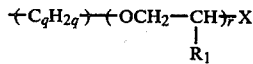

where

X is hydroxy, alkoxy, aralkoxy, acyloxy or organosiloxy,
$R_1$ is as previously defined,
q is an integer from 1 to 4, and
r is an integer from zero to 4;
R" is hydrogen, X or

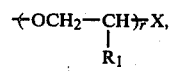

where $R_1$, r and X are as previously defined; and s is zero or one;
provided that if s is zero then in at least one occurrence R' is not hydrogen, or if s is one then in at least one occurrence at least one of either R' or R" is not hydrogen.

The compounds have been found to be particularly suited for use as components for functional fluids such as hydraulic fluids and heat-transfer fluids.

DETAILED DESCRIPTION OF THE INVENTION

The novel 1,3-dioxane and dioxolane derivatives of the invention are suitably produced by reaction of a polyhydroxyl compound with reactive cyano-substituted compounds of a formula corresponding to the desired cyclic compound. Specifically, such reactive cyano-substituted compounds may include reactive carbonyl- or dialkoxy-containing compounds of the formula

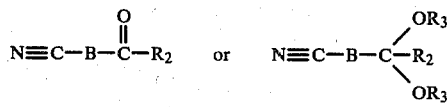

wherein B is as previously defined, $R_2$ is hydrogen, phenyl, or a monovalent radical of from 1 to 10 carbons selected from branched or linear alkyl and cyano- or hydroxy-substituted derivatives thereof, and $R_3$ is $C_{1-4}$ alkyl. Preferably, $R_2$ is hydrogen or methyl, and B is $C_{2-6}$ straight or branched alkylene.

The polyhydroxyl compounds for use in forming the compounds of the invention are 1,2- or 1,3-dihydroxy-substituted aliphatic compounds additionally substituted with hydroxyalkyl substituents or derivatives thereof. Suitable derivatives of hydroxyalkyl substituents are those formed by reaction of the hydroxy moiety with common reactive substances capable of replacing the hydrogen. Included are substituents wherein the hydroxy is replaced by alkoxy, aralkoxy, acyloxy, organosiloxy, as well as (poly)alkylene oxide extended ether derivatives thereof terminating with the previously mentioned alkoxy, aralkoxy, hydroxyalkoxy, acyloxy or organosiloxy substituents. Such compounds and the processes for making them are well-known in the art and correspond to either of the following formulas:

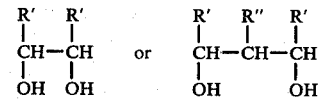

wherein R' and R" are as previously defined and at least one of R' or R" is not hydrogen.

An additional suitably employed polyhydroxyl compound is glycerine, which in view of its widespread commercial availability is a preferred polyhydroxyl reactant.

The following polyhydroxyl compounds are illustrative of those suitably employed in forming the instant invented compounds.
glycerine;
1,2,4-trihydroxy butane;
1,2,4-trihydroxy pentane;
1,2,5-trihydroxy pentane;
1,2-dihydroxy-3-(2-hydroxyethoxy)propane;
1,2-dihydroxy-3-(hydroxypropyleneoxy)propane;
1,2-dihydroxy-3-[hydroxy(poly)alkyleneoxy]propanes, such as
 1,2-dihydroxy-3-[hydroxydi(ethyleneoxy)]propane, 1,2-dihydroxy-3-[hydroxydi(propyleneoxy)]propane,
1,2-dihydroxy-3-(hydroxyethyleneoxypropyleneoxy)propane, etc.;
1,2-dihydroxy-3-alkoxy propanes, such as
1,2-dihydroxy-3-methoxy propane,
1,2-dihydroxy-3-tertiary butoxy propane,
1,2-dihydroxy-3-sec-butoxy propane, etc.;
1,2-dihydroxy-3-[alkoxy(poly)alkyleneoxy]propanes, such as
1,2-dihydroxy-3-[methoxydi(ethyleneoxy)]propane,
1,2-dihydroxy-3-[ethoxydi(propyleneoxy)]propane,
1,2-dihydroxy-3-[butoxydi(ethyleneoxy)propoxy]propane, etc.;
1,2-dihydroxy-3-acyloxypropanes, such as
1,2-dihydroxy-3-(acetyloxy)propane,
1,2-dihydroxy-3-(propionyloxy)propane, etc.;
1,2-dihydroxy-3-[acyloxy(poly)alkyleneoxy]propanes, such as
1,2-dihydroxy-3-(acetyloxyethoxy)propane,
1,2-dihydroxy-3-(acetyloxyethyleneoxypropyleneoxy)propane,
1,2-dihydroxy-3-[benzoyloxy(ethyleneoxy)]propane, etc.;
1,2-dihydroxy-3-organosiloxypropanes, such as
1,2-dihydroxy-3-(trimethylsiloxy)propane,
1,2-dihydroxy-3-(trimethoxysiloxy)propane, etc.;
1,2-dihydroxy-3-[organosiloxy(poly)alkyleneoxy]propanes, such as
1,2-dihydroxy-3-[(triethylsiloxy)ethyleneoxypropyleneoxy]propane,
1,2-dihydroxy-3-[(triphenylsiloxy)di(ethyleneoxy)]propane,
1,2-dihydroxy-3-[(trimethoxysiloxy)tri(ethyleneoxy)]propane, etc.;
1,3-dihydroxy-substituted compounds, such as:
1,3,5-trihydroxypentane,
1,3-dihydroxy-2-methoxypropane,
1,3-dihydroxy-2-(2-hydroxyethoxy)propane,
1,3-dihydroxy-2-(2-methoxyethoxy)butane,
1,3-dihydroxy-2-(2-hydroxyethoxy)butane,
1,3-dihydroxy-4-(2-methoxyethoxy)butane,
1,3-dihydroxy-4-(hydroxyethyleneoxypropyleneoxy)butane,
1,3-dihydroxy-5-[(trimethoxysiloxy)di(propyleneoxy)]pentane, etc.; and so forth.

The reaction may suitably be carried out in the presence of a catalytically effective amount of an acidic catalyst, for example, sulfonic acid, sulfonic acid resin or other strong acid or strong acid resin that adequately catalyzes this type of reaction. Molar ratios of catalyst to reactive cyano-substituted reactant from about 0.0001/1.0 to about 0.1/1.0, preferably from about 0.001/1.0 to about 0.05/1.0 may be used.

It is convenient to conduct the reaction in a solvent, preferably such a solvent that readily forms an azeotropic mixture with water or lower alkanols allowing for the rapid removal of the by-product water or lower alkanol formed during the reaction. Further preferred are such solvents that additionally do not form such azeotropic mixtures with either of the reactants. Examples of suitable solvents include benzene, toluene, petroleum ether, chlorinated aliphatic solvents, etc.

The reaction may also be conducted without a solvent in which case the water or lower alcohol formed during the reaction may be removed by direct distillation preferably at reduced pressure and temperature to limit the formation of oligomers which may form at elevated temperatures.

The reaction is conducted at temperatures from about 0° C. to about 200° C. depending on the reactants, pressures, and other process conditions employed.

The required reaction time will vary depending on the reactants and process conditions employed. Generally reaction times from about 1 to about 48 hours suffice to convert substantially all of one starting reactant employed in limiting quantities.

Either reactant may be employed in large excess. Molar ratios of cyano-substituted reactant to polyhydroxyl compound ranging from about 20/1 to about 1/20 are operable. Preferably, in order to avoid separation of large volumes of unreacted compounds the reactants are combined in nearly equal molar proportions, for example in a molar range from about 2/1 to about 1/2. Most preferred is a range from about 1.2/1.0 to about 1.0/1.2. An excess of the lower boiling reactant whether polyhydroxyl compound or cyano-substituted reactant may be employed to insure substantially complete reaction of the higher boiling reactant. This procedure simplifies later distillative separation of the cyclic product from reactants by providing a mixture of components having the maximum difference in boiling points.

It is of course also suitable to add the nitrile substituent to a previously formed cyclic compound to produce the desired substituted compounds. Accordingly, a compound containing terminal ethylenic unsaturation instead of a cyano substituent but otherwise similar to the previously identified reactive carbonyl- or dialkyl-containing compound may be reacted with one of the previously identified polyhydroxyl compounds. Contacting the cyclic reaction product which contains an unsaturated alkyl substituent with hydrogen chloride results in formation of the corresponding chloro-alkyl-substituted cyclic compound which may then be reacted with sodium cyanide to form the desired product. This alternate procedure is further illustrated in Example 3.

Under some circumstances the reaction may produce a mixture of products. For example, because glycerine contains three reactive hydroxyl substituents in close proximity, both of the corresponding 1,3-dioxolane and 1,3-dioxane derivatives may be produced. Separation of such a mixture of products, if desired, may be accomplished by careful fractional distillation.

A further alternative procedure for forming the above compounds wherein X is not hydrogen is to first produce the desired cyanoalkyl-substituted cyclic compound that is further ring-substituted with hydroxy or hydroxy-alkyl substituents. The hydrogen of these reactive hydroxy-containing substituents is replaced with X, the remnant of a reactive substance capable of replacing hydrogen by well-known techniques. For example, by use of a Williamson synthesis alkoxy and aralkoxy moieties may be substituted for hydroxy. Similarly reactions with alkylene oxides, glycidyl ethers or mixtures thereof may be used to form an ether functionality producing hydroxy-substituted alkoxy or polyalkyleneoxy substituents. Further substituents are, for example, acyloxy moieties formed by condensation of the hydroxyl-substituted cyclic compounds with an acid halide such as acetyl chloride and organosiloxy derivatives such as those formed by condensation of the hydroxyl-substituted cyclic compound with a halo-substituted organosilane, e.g., trimethylchlorosilane or trimethoxychlorosilane. By the same procedure alkoxy, organosiloxy and acyloxy functionality may be introduced into substituent R by functionalization of a hydroxyl moiety of $R_2$. By the term organosiloxy is included the well-known lower alkyl- or phenyl-substituted siloxy radicals as well as lower alkoxy- or phenoxy-substituted siloxy radicals.

SPECIFIC EMBODIMENTS

The following examples are provided as further illustrative of the present invention and are not to be construed as limiting.

EXAMPLE 1

A solution of 5-oxohexanenitrile (375 g, 3.4 moles), glycerine (248 g, 2.7 moles), p-toluenesulfonic acid (0.5 g, 0.0027 mole) and toluene (200 ml, solvent) were placed in a 1000 ml round-bottom flask and heated to reflux. Water was removed azeotropically and collected in a Dean-Stark apparatus. Within 24 hours, 42 ml $H_2O$ had been collected and analysis by gas chromatography indicated that 84 percent of the glycerine had been converted. An additional 46 g glycerine (0.5 mole, total 3.2 moles) was added. After 48 hours, 58 ml $H_2O$ was collected and analysis indicated 98.7 percent conversion of glycerine. The solution was cooled to 60° C., basified with $NaHCO_3$ and filtered. The solvent, toluene, and unreacted 5-oxohexanenitrile were removed by vacuum distillation through a 15-plate Oldershaw column (200 mm and 100 mm Hg, respectively). The product consisted almost entirely of 2-methyl-2-(3-cyanopropyl)-4-hydroxymethyl-1,3-dioxolane which was then distilled overhead (B.P. 171.5° C./7 mm Hg) yielding a clear, colorless liquid. All samples of >97 percent purity were combined giving a final product of 98.5 percent purity. Isolated yield was 75 percent.

EXAMPLE 2

A 200-ml flask was charged with 819 g of 4,4-dimethoxybutane nitrile and 584 g of glycerine. The mixture was acidified with methane sulfonic acid (3.2 g) and stirred at 20° C. until homogenous. The mixture was heated to about 56° C. under vacuum (about 1 Torr) to remove methanol. Heating was continued until no further methanol was collected (about 1 hour).

The acid was neutralized by adding triethylamine (7.6 g) and the reaction mixture distilled under vacuum employing a Vigreaux distillation column. Product fractions having a boiling point range from 117° C. to 137° C. (0.1 Torr) were obtained. Analysis by vapor phase chromatography, nuclear magnetic resonance spectroscopy and infrared absorption spectroscopy indicated the product consisted of a mixture of 2-(2-cyanoethyl)-4-hydroxymethyl-1,3-dioxolane and 2-(2-cyanoethyl)-5-hydroxy-1,3-dioxane. Total distilled yield was 938 g.

EXAMPLE 3

Anhydrous hydrogen chloride was bubbled into a solution of about 368 g of glycerine in 300 ml chloroform cooled to a temperature of −14° C. While maintaining a slight positive pressure, 168 g of acrolein was added dropwise with stirring over a 90-minute period. The temperature was maintained below −10° C. and hydrogen chloride addition continued with stirring for an additional hour.

The reaction was allowed to warm to room temperature whereupon a cloudy suspension remained which upon standing separated into two layers. The lower layer containing the glycerine reaction product was drawn off, neutralized with about 3 ml of triethylamine and washed with about 50 ml of saturated sodium carbonate solution. The organic layer was again separated, dried over calcium sulfate and heated in vacuo to remove residual acrolein and chloroform. Final vacuum distillation yielded a mixture of 2-(2-chloroethyl)-4-hydroxymethyl-1,3-dioxolane and 2-(2-chloroethyl)-5-hydroxy-1,3-dioxane.

A portion of the mixture was then combined in ethylene glycol monomethyl ether with an equal molar quantity of sodium cyanide. The mixture was refluxed at 125° C. for approximately 8 hours. The mixture was cooled and the salt separated by filtration. Vacuum distillation of the filtrate yielded a clear light colored liquid identified by GC-mass spectrometry and nuclear magnetic resonance spectrometry as a mixture of 2-(2-cyanoethyl)-4-hydroxymethyl-1,3-dioxolane and 2-(2-cyanoethyl)-5-hydroxy-1,3-dioxane.

EXAMPLE 4

Trimethylsilane Derivative

Trimethylchlorosilane (109 g) was added dropwise to a stirred solution containing 116 g of the acetal mixture produced in Example 2, 79 g of pyridine acid acceptor and 454 g of diethylether solvent. The temperature was maintained at 20° C.–25° C. with an ice bath. The trimethylchlorosilane was added over a period of 1 hour. After 30 minutes additional stirring the reaction products were cooled to about −10° C. and the pyridine hydrochloride formed during the reaction was removed by filtration. The remaining liquor was washed with two 100 ml volumes of water and the ether stripped under vacuum. Distillation of the product mixture using a Vigreaux distillation column (2.5 cm×20 cm) gave 140.3 g of product having a boiling point from 95° C.–98° C. (0.5 Torr). The product formed was a mixture of 2-(2-cyanoethyl)-4-(trimethylsiloxymethyl)-1,3-dioxolane and 2-(2-cyanoethyl)-5-(tri-methylsiloxy)-1,3-dioxane.

EXAMPLE 5

Acetate Derivative

A mixture of acetyl chloride (3.8 g) and 5.0 g of triethylamine acid acceptor were added over a 10-minute period at room temperature to a rapidly stirred mixture comprising 5.4 g of the acetal mixture produced in Example 2 and 14.5 g of diethylether solvent. Ether which was lost during the exothermic reaction was replaced and the thick slurry resulting from the reaction was filtered to remove triethylamine hydrochloride.

A clear, orange colored product remained. The ether solvent was stripped under vacuum to yield 4.7 g of crude product which remained a liquid under ambient conditions. Absorption bands at 2260 $cm^{-1}$ and 1740 $cm^{-1}$, characteristic of nitrile and ester functionality, respectively, were observed. Further identification by nuclear magnetic resonance spectroscopy was also made. The product was a mixture of 2-(2-cyanoethyl)-4-acetoxymethyl-1,3-dioxolane and 2-(2-cyanoethyl)-5-acetoxy-1,3-dioxane.

What is claimed is:
1. A compound of the formula

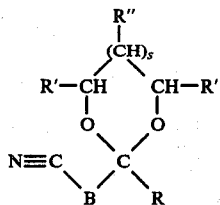

wherein
R is hydrogen, phenyl, or a monovalent radical of from 1 to 10 carbons selected from the group consisting of branched or linear alkyl and cyano-, hydroxy-, alkoxy-, acyloxy-, and organosiloxy-substituted derivatives thereof;

B is a divalent radical of from 2 to 10 carbons selected from the group consisting of branched or linear alkylene and $-(CH_2)_m-OCH_2CH(R_1)-_n$, where $R_1$ is hydrogen, methyl or ethyl, and m and n are integers equal to or greater than one;

R' independently each occurrence is selected from the group consisting of hydrogen and $C_qH_{2q}X$, where q is an integer from 1 to 4, and X is hydroxy, acyloxy, organosiloxy or

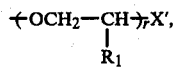

where r is an integer from 1 to 4, X' is hydroxy, alkoxy, aralkoxy, acyloxy or organosiloxy, and $R_1$ is as previously defined;

R" is hydrogen or X; and s is zero or one;

provided that if s is zero then in at least one occurrence R' is not hydrogen, or if s is one then in at least one occurrence at least one of either R' or R" is not hydrogen.

2. A compound or mixture thereof according to claim 1 wherein R is hydrogen or methyl and B is $C_{2-6}$ branched or linear alkylene.

3. A compound or mixture thereof according to claim 2 wherein X is hydroxy, acyloxy, or organosiloxy.

4. A compound according to claim 3 that is 2-(2-cyanoethyl)-4-hydroxymethyl-1,3-dioxolane, 2-(2-cyanoethyl)-5-hydroxy-1,3-dioxane or a mixture thereof.

5. A compound according to claim 3 that is 2-methyl-2-(3-cyanopropyl)-4-hydroxymethyl-1,3-dioxolane.

6. A compound according to claim 3 that is 2-(1,1-dimethyl-3-cyanopropyl)-4-hydroxymethyl-1,3-dioxolane, 2-(1,1-dimethyl-3-cyanopropyl)-5-hydroxy-1,3-dioxane or a mixture thereof.

7. A compound according to claim 3 that is 2-(2-cyanoethyl)-4-trimethylsiloxymethyl-1,3-dioxolane, 2-(2-cyanoethyl)-5-trimethylsiloxy-1,3-dioxane or a mixture thereof.

8. A compound according to claim 3 that is 2-(2-cyanoethyl)-4-acetoxymethyl-1,3-dioxolane, 2-(2-cyanoethyl)-5-acetoxy-1,3-dioxane or a mixture thereof.

* * * * *